United States Patent [19]

Ryan

[11] Patent Number: 4,788,139

[45] Date of Patent: Nov. 29, 1988

[54] PLATELET AGGREGATION REAGENT, REAGENT CONTAINER AND METHOD OF DETERMINING PLATELET AGGREGATION IN EDTA-ANTICOAGULATED BLOOD

[75] Inventor: Wayne L. Ryan, Omaha, Nebr.

[73] Assignee: Streck Laboratories, Inc., Omaha, Nebr.

[21] Appl. No.: 82,233

[22] Filed: Aug. 6, 1987

[51] Int. Cl.$^4$ ................................................ C12Q 1/56
[52] U.S. Cl. .......................................... 435/13; 435/4; 435/29; 435/2; 436/69; 424/101
[58] Field of Search .......................... 435/2, 4, 29, 13; 436/69

[56] References Cited

U.S. PATENT DOCUMENTS 3,989,382 11/1976 Kent et al. ............................ 436/69
4,145,185 3/1979 Brinkhous et al. ................... 436/69

OTHER PUBLICATIONS

Kowa-Chem. Abst., vol. 96 (1982), p. 196174j.

Primary Examiner—Sam Rosen
Attorney, Agent, or Firm—Larson and Taylor

[57] ABSTRACT

A platelet aggregation reagent for EDTA-anticoagulated blood comprises calcium chloride, sodium citrate and a platelet-aggregating agent; the calcium chloride and the sodium citrate being present in a proportion of about 1.5 micromoles: 5 micromoles to about 7.5 micromoles: 2.5 micromoles per at least about a platelet aggregating amount of the agent.

A platelet aggregation reagent container for EDTA-anticoagulated blood comprises an elongated container suitable for use in a platelet counter containing a reagent comprising about 1.5 micromoles to 7.5 micromoles of calcium chloride, about 2.5 micromoles to 5.0 micromoles of sodium citrate, and at least about a platelet aggregating amount of a platelet aggregating agent.

A method of determining platelet aggregation in EDTA-anticoagulated blood, comprises counting the number of platelets contained in an EDTA-anticoagulated blood sample to obtain an initial platelet count (IC), contacting the sample with calcium chloride, sodium citrate and a platelet-aggregating agent in proportions of at least about a platelet aggregating amount of the agent per about 450 microliters of the samples and about 1.2 micromoles to 7.5 micromoles of the calcium chloride and about 2.5 micromoles to 5.0 micromoles of the citrate, counting the number of platelets contained in the thus contacted sample at desired intervals for a period of about 1 minute to 10 minutes, selecting the maximum platelet count (MC) obtained in step (c) and calculating platelet aggregation (PA) from the equation $$PA = [(IC - MC)/IC].$$

22 Claims, No Drawings

PLATELET AGGREGATION REAGENT, REAGENT CONTAINER AND METHOD OF DETERMINING PLATELET AGGREGATION IN EDTA-ANTICOAGULATED BLOOD

BACKGROUND OF THE INVENTION

1. Field of the Invention

This invention relates to a platelet aggregation reagent for EDTA-anticoagulated blood, a reagent container and a method of measuring platelet aggregation using a standard platelet counter which is cost-effective, simple, overcomes storage problems and can be applied for routine analysis utilizing very small samples.

2. Description of the Background

Platelets play an important role in coagulation. Although their ability to function properly is affected by many common drugs such as aspirin, the proper functioning of platelets is not routinely tested because no cost-effective tests exist at the present time.

When an injury occurs, platelets adhere to the damaged tissue and a platelet aggregate or platelet plug is then formed. Coagulation is initiated thereafter, ultimately leading to fibrin formation which strengthens the platelet plug.

The activation of platelets and their response play a key role in hemostasis. At present, the number of platelets in the blood is routinely measured by means of hematology counting instruments. Although the number of platelets varies considerably from person to person, these variations are of little importance as long as platelet function is preserved. For example, a platelet count of 150,000–400,000/mm$^3$ is normal but adequate platelet function can be observed even at counts as low as 50,000/mm$^3$.

Platelet counts, which are done routinely, are probably of less importance than platelet function which is rarely done. However, in practice, many more platelet counts than platelet function tests are performed. This is most likely due to the development of routine systems for counting platelets whereas methods for measuring platelet function are tedious and expensive. By means of example, a platelet function test may cost thirty times more than a platelet count (about $5.00 vs. $150.00).

There are many instances where testing platelet function would be of use. These are cases of either hereditary conditions in which there is a genetic absence of some part of the system, or situations where the interference occurs in the steps leading to activation of the platelets.

Examples of hereditary platelet disorders are afibrinogenemia, Bernard-Soulier syndrome, connective tissue abnormalities, Glanzmann's thrombasthenia, glycogen storage disease, macrothrombocytothia, nephritis and deafness, homocystinuria, May-Hegglin anomaly, dystrophia myotonica, storage pool defects including Chediak-Higashi syndrome, thrombocytopenia with absent radi, Wiskott-Aldrich syndrome and Hermansky-Pedlak syndrome, Wilson's disease, and swiss cheese platelets, among others.

In addition, there also exist acquired platelet disorders. Examples of acquired platelet disorders are aspirin ingestion, asthma, hypothyroidism, ethanol-induced, hypercoagulability, immune thrombocytopenia, lupus erythematosus, myeloproliferative disorders including myeloid metaplasia polycythemia rubra vera, scurvy, idiopathic thrombocytopenia purpura, sideroblastic anemia, thrombocythemia, Von Willebrand's syndrome, uremia and abnormal release mechanism (aspirin-like defect), among others.

Most notable among the acquired disorders is that resulting from ingestion of aspirin. In addition there is a large number of other drugs that interfere with platelet function However, none is more ubiquitous than aspirin.

Various methods have been known for measuring platelet function. Among them, is aggregometry which is described by Born, G. B. R., in "Quantitated Investigations into the Aggregation of Blood Platelets", J. Physiol.162:67–68(1962).

Aggregometry is a turbidometric method for measuring platelet aggregation. Platelet-rich plasma is prepared from whole blood by centrifugation to remove the red blood cells. The platelets are placed in a cuvette at 37° C. with a stirrer, and a platelet activator such as collagen is added to induce platelet aggregation. The aggregation of the platelets reduces the turbidity of the platelet suspension and more light passes through the cuvette. Changes in transmitted light are recorded as a voltage change on a chart on a chart recorder.

Cardinal D. C., and Flower, R. J., in "The Electronic Aggregometer: a Novel Device for Assessing Platelet Behavior in Blood", J. Pharmacol. Methods 3:135–158(1980) describe a method of measuring aggregation by impedance. This is a relatively new method utilizing whole blood. In this method, aggregation is measured as changes in impedance which occur as platelets aggregate on platinum electrodes.

Methods using platelet counters are the most aoourate for measuring platelet aggregation since only single platelets are counted (perhaps doublets).

Malinski, J. A., and Nelsestuen, G. L., in "Relationship of Turbidity to the Stages of Platelet Aggregation", Biochim. et Biophys. Acta 882:177–182(1986), have shown that small aggregates of platelets give increased instead of decreased turbidity in an aggregometer. In this method, very large aggregates are required to produce a decrease in light scattering. Therefore, turbidity can increase or decrease with platelet aggregation depending on the size of the aggregates. Thus, it is argued in the reference, aggregometry is subject to variations that result from the size of the aggregates. Platelet counters, on the contrary, are not subject to these interpretive difficulties.

The use of platelet counters to measure platelet aggregation has been discussed by several authors (Higashi, T., Hashimoto, M., Kakishita, E., and Nagai, K., in "The Changes in the Number of Single Platelets in Human and Rabbit Platelet Aggregation Measured by Electric Particle Counting Method", Thrombosis Res. 21:457–468(1981); Butchers, J., Humphrey P. P. A., Hyde, J. J., Lumley, P., and Spurling, N. W., in "The Evaluation of a New Electronic Counting Technique for Measurement of Platelet Aggregation in Human Whole Blood in vitro", British J. Pharmacol. 70:160–161(1980); Saniabadi, A. R., Lowe, G. D. O., Forbes, C. D., Prentice, C. R. M., and Barbenel, J. C., in "Platelet Aggregation Studies in Whole Human Blood," Thrombosis Res. 30:625–632(1983); Lumley, P., and Humphrey, P. A., in "A Method for Quantitating Platelet Aggregation and Analyzing Drug-receptor Interactions on Platelets in Whole Blood in vitro", J. Pharmacol. Methods 6:153–166(1981)).

The method used by these investigators consists of warming blood or plasma in a water bath at 37° C. and stirring with a magnetic stirrer. Blood for this procedure is collected in sodium citrate which causes spontaneous platelet aggregation. It has been reported that in as short a period as 40 minutes, 40% of the platelets may be lost (Fox, S. C., Burgess-Wilson, M., Heptinstall, S., and Mitchell, J. R. A., in "Platelet Aggregation in Whole Blood Determined Using the Ultra-Flo 100 Platelet Counter", Thromb. Haemostas. (Stuttgart) 48:327-329(1982)). This results in problems of storage and collection.

Accordingly, there is still a need for an improved method of testing platelet function which is reliable, cost-effective and easy to implement with readily available instrumentation while at the same time overcoming storage problems encountered by prior art procedures.

SUMMARY OF THE INVENTION

This invention relates to a platelet aggregation reagent for EDTA-anticoagulated blood, said reagent comprising
 calcium chloride,
 sodium citrate, and
 a platelet-aggregating agent; the calcium chloride and the citrate being present in a proportion of from about 1.5 micromole:5 micromoles to about 7.5 micromoles:2.5 micromoles per at least about a platelet aggregating amount of the agent.

This invention also relates to a platelet aggregation reagent container for EDTA-anticoagulated blood, comprising
 an elongated container suitable for use in a platelet counter, said container containing a reagent comprising
 about 1.5 micromoles to 7.5 micromoles of calcium chloride;
 about 2.5 micromoles to 5.0 micromoles of sodium citrate; and
 at least about a platelet aggregating amount of a platelet-aggregating agent.

The invention also relates to a method of determining platelet aggregation in EDTA-anticoagulated blood, said method comprising (a) counting the number of platelets contained in an EDTA-anticoagulated blood sample to obtain an initial platelet count (IC);

(b) contacting the sample with calcium chloride, sodium citrate and a platelet aggregating agent in proportions of at least about a platelet aggregating amount of the agent per about 450 microliters of the sample, about 1.2 micromoles to 7.5 micromoles of the calcium chloride, and about 2.5 micromoles to 5.0 micromoles of the citrate;

(c) counting at desired intervals for a period of about 1 minute to 10 minutes the number of platelets contained in the thus contacted sample;

(d) selecting the maximum platelet count (MC) obtained in step (c); and (e) calculating platelet aggregation (PA) from the equation $$PA = (IC - MC)/IC.$$

The system described herein permits the measurement of platelets in EDTA-anticoagulated blood and is therefore useful for a variety of coagulation tests such as those for platelet factor 3 assays, platelet retention, factor assays, prothrombin time and partial thromboplastin time, among others.

A more complete appreciation of the invention and many of the attendant advantages therein will be readily preceived as the same becomes better understood by reference to the following detailed description. Other objects, advantages and features of the present invention will also become apparent to those skilled in the art from the following discussion.

DESCRIPTION OF THE PREFERRED EMBODIMENTS OF THE INVENTION

The present invention came about as a result of the desire of the inventors to overcome the drawbacks of the prior art platelet aggregation tests and to develop a method for measuring platelet aggregation that uses a standard platelet counter, overcomes storage problems and simplifies operations for routine analysis.

As already indicated above, platelets are unstable in citrated blood. In addition, blood samples collected in citrate are unsuitable for the measurement of a variety of other parameters.

Moreover, blood is collected from most procedures, with the exception of coagulation studies, in potassium ethylenediamine tetraacetic acid (EDTA). However, platelets become inactive in EDTA-anticoagulated blood and their function cannot be measured in these solutions.

Neither anticoagulant is useful at this point in time for all hematological procedures. However, the collection of blood in EDTA tubes is the most desirable of the two given the stability of the platelets in the presence of EDTA. Additionally, the use of EDTA-anticoagulated blood for measuring platelet function would eliminate the need to collect several tubes from a patient and permit the measurement of various parameters with the same sample.

Another advantage of the present method is the small volume of blood sample required for testing platelet function. A large volume of blood is required for measuring platelet aggregation by aggregometry. Usually, a 10.0 ml sample is drawn from a patient. Drawing such volume is on occasion a problem with infants or children.

The present invention also provides a significant reduction in the expenditures. The price of an aggregometer oscilates between $5,000 and $15,000. Due to its high cost, not many laboratories can afford to have one. The present invention, on the contrary, can be conducted with the aid of inexpensive platelet counting equipment which is found in almost all clinical laboratories and is routinely used for platelet counting, white blood count and red blood count, among others.

The inventors have demonstrated that by adding calcium and citrate ions to an EDTA-anticoagulated blood sample they can reverse the inactivating effect that EDTA has on the platelets contained in the blood.

The inventors set out to study the differences in the effect on platelet function brought about by the addition of citrate and EDTA to a blood sample (see Example 1) and the potential routes to overcome the inactivation of platelet function caused by the presence of EDTA in the sample.

In an attempt to reverse the inactivating effect of EDTA on platelet function, several levels of calcium ion were added to the EDTA-anticoagulated blood. Surprisingly, the inventors found that the presence of calcium ions within a certain range of concentrations acted to reverse the inhibition of platelet function caused by the EDTA.

The optimal concentration of calcium chloride was found to be about 3 microliters to 15 microliters of 0.5 M calcium chloride per 450 microliters of EDTA-anticoagulated whole blood. More than this amount produces inhibition of aggregation.

In addition, if excess calcium is added and the sample is allowed to sit for approximately ten minutes before conducting the test, clotting is observed. Clotting may also occur at levels of calcium below the disclosed range. This efffct varies somewhat with different samples. Clearly, when clotting occurs it is not possible to measure platelet aggregation (see Example 2).

Thus, sodium citrate is added to the sample to avoid clotting. Surprisingly, the inventors found that a range of about 5 microliters to 10 microliters of 0.5 M sodium citrate is adequate to prevent blood clotting in the samples. Above 10 microliters, aggregation is inhibited by the sodium citrate (see Example 3).

In order to measure the aggregation of platelets, an "agonist" is added to the reagent composition in at least about a platelet aggregating amount.

A variety of agents capable of aggregating platelets or acting as "agonists" for platelet aggregation are known in the art. Examples of such agents are collagen, adenosine diphosphate (ADP), epinephrine, ristocetin, adrenaline, thrombin and arachidonic acid, among others. These agents are used in amounts about at least capable of inducing platelet aggregation.

In particular, ADP may be used in an amount of about 10 micromoles to 30 micromoles per 450 microliters of EDTA-anticoagulated blood. Collagen may be used in an amount of about 0.1 mg/ml to 0.4 mg/ml, epinephrine may be used in an amount of about 5 micromoles to about 20 micromoles, and ristocetin may be utilized in an amount of about 1.0 mg/ml to 1.5 mg/ml of EDTA-anticoagulated blood.

The calcium chloride and the sodium citrate are present in the composition in a proportion of from about 1.5 micromoles:5 micromoles to about 7.5 micromoles:2.5 micromoles for a least a platelet aggregating amount of the "agonist". A preferred proportion of the calcium chloride and sodium citrate in the composition is about 2.5 micromoles:5 micromoles.

The platelet aggregation reagent may suitably be in the form of a solid, and preferably in the form of a powder. Preferably the reagent is prepared by mixing and lyophilizing the components.

A preferred form of preparing the composition of this invention is by diluting about ten fold a solution of calcium chloride and a solution of sodium citrate containing the desired amounts of the components, mixing them along with the aggregation-inhibiting agent, and lyophilizing the mixture and sealing the tube which is then ready for use (see Example 4).

This invention also provides a platelet-aggregation reagent container for EDTA-anticoagulated blood comprising an enlongated container suitable for use in a platelet counter comprising about 1.5 micromoles to 7.5 micromoles of calcium chloride;

about 2.5 micromoles to 5.0 micromoles of sodium citrate; and at least about a platelet-aggregating amount of a platelet-aggregating agent.

Suitably, the platelet-aggregating agents are "agonists" such as those described above and can be utilized in amounts as already described.

The platelet-aggregation reagent container may be manufactured by mixing the components in the container and then lyophilizing and sealing the container.

In a preferred form, the platelet-aggregation reagent container is disposable and may be produced from a low cost material such as plastic or inexpensive glass. An example of this is a test tube or a cuvette.

This invention also provides a method of determining platelet aggregation in EDTA-anticoagulated blood, said method comprising (a) counting the number of platelets contained in an EDTA-anticoagulated blood sample to obtain an initial platelet count (IC);

(b) contacting the sample with calcium chloride, sodium citrate and a platelet aggregating agent in proportions at least about a platelet aggregating amount of the agent per about 450 microliters of sample, about 1.2 micromoles to 7.5 micromoles of the calcium chloride and about 2.5 micromoles to 5.0 micromoles of the citrate;

(c) counting at desired intervals for a period of about 1 minute to 10 minutes the number of platelets contained in the thus contacted sample;

(d) selecting the maximum platelet count (MC) obtained in step (c); and (e) calculating platelet aggregation (PA) from the equation $$PA = (IC - MC)/IC.$$

In a preferred form of the method, step (e) above is conducted by calculating the percent platelet aggregation (% PA) from the equation $$\% PA = [(IC - MC) \times 100]/IC.$$

However, other forms of expressing the amount of platelet aggregation in a sample are also contemplated within the confines of this invention.

After the addition of the blood sample to the platelet-aggregating composition of the invention, the number of platelets contained in the sample mixture is suitably measured at intervals, e.g., every two minutes. In general, a good reading of platelet count can be obtained within a period of about 10 minutes from the time of the mixing. Preferablly, the platelet count is taken for a period of about six to eight minutes.

The use of EDTA as an anticoagulant for the blood sample permits the storage of blood samples for several hours without any appreciable loss of platelets through aggregation (or loss of platelet function). The EDTA, in fact, makes the platelets more stable.

The inventors surprisingly found that EDTA-anticoagulated blood samples could be made to recover platelet activity even after a period of storage of up to about six hours after collection (see, Example 5).

The present invention is reliable and accurate to the extent at least that standard aggregometry has been shown to be. A good agreement with all aggregation-inducing agents or "agonists" has been shown for a large number of samples (see, example 6).

This invention has been shown to yield reliable results when a decrease in the platelet count occurs as well. Such is the case when a normal subject ingests aspirin. A good correspondence has been found between the results obtained by the present method and those obtained with an aggregometer before aspirin ingestion.

However, after aspirin ingestion the present method showed a decrease in platelet aggregation whereas no such decrease was seen in the results obtained with the prior art aggregometer method. This is attributed to the fact that the plasma sample is continually being stirred in the aggregometer and this seems to enhance the ability of the platelets to aggregate. No lowering of aggregation was observed when the samples were continually mixed in the present method (see, Example 7).

The present invention has also been shown to be useful for determining platelet aggregation in samples of abnormal subjects such as myeloma patients. Patients diagnosed with multiple myeloma are known to show decreased platelet aggregation with the "agonists" collagen and epinephrine whether or not they are taking medications.

This was corroborated by using the present system. However, the data obtained with a prior art aggregometer method did not show this reduction. When the samples measured by the present method were continually mixed as is done in the aggregometer method, the observed decrease in aggregation was lost. Again this shows that loss of sensitivity occurs when utilizing an aggregometer due to the constant mixing required (see, Example 8).

The inventors have also shown that the present platelet function test system may be utilized for the purpose of determining prothrombin time (P.T.) and partial thromboplastin time (P.T.T.) (see, Example 9).

Having know generally described this invention, the same will be better understood by reference to certain specific examples which are included herein for purposes of illustration only and are not intended to be limiting of the invention or any embodiment thereof, unless so specified.

EXAMPLES

EXAMPLE 1

Aggregation of Platelets in Citrated- vs. EDTA-anticoagulated Blood

Two samples are prepared in order to test the aggregation of platelets in citrated blood and EDTA-anticoagulated blood. Collagen (Sigma) is then added to the samples and the platelet count is determined at various times thereafter on a Cell Dyn 900 platelet counter. The results are shown in Table 1 below. The tubes used are Vacutainer ® and contain 15 mg of EDTA ($K_3$) or 3.2% buffered citrate solution. The reconstituted concentration is 2 mg/ml. The initial platelet count is 207,000.

TABLE 1

| Aggregation of Platelets in Citrate vs. EDTA Anticoagulant | | | | | |
|---|---|---|---|---|---|
| Inactivation by EDTA | Platelet Count ($\times 10^3/mm^3$) | | | | % Aggregation |
| | 0 | 1 min | 2 min | 3 min | |
| 450 ul citrated whole blood 50 ul collagen | 11 | 3 | 0 | 0 | 100% |
| 450 ul $K_3$-EDTA whole blood 50 ul collagen | 207 | 220 | 230 | 219 | 0% |

EXAMPLE 2

Calcium Activation of Platelets in EDTA-anticoagulated Blood

Calcium is added to reverse the inactivating effect of potassium-EDTA on platelets. Several concentrations of calcium ions are tested on a Cell Dyn 900 counter as is shown in the leftmost column of Table 2 below.

Although only the results from the 2 mg/ml collagen (Sigma) activation of platelet aggregation are shown in the table, similar results are obtained when ADP is utilized to initiate platelet aggregation. The concentration of the $CaCl_2$ solution added is 0.5 M.

TABLE 2

| Calcium Activation of Platelets in EDTA-anticoagulated Blood | | | | | |
|---|---|---|---|---|---|
| | Platelet Count ($\times 10^3/mm^3$) | | | | % Aggregation |
| | 0 | 1 min | 2 min | 3 min | |
| 3.0 ul $CaCl_2$ 450 ul EDTA Blood 50 ul collagen | 287 | 250 | 230 | 235 | 0% |
| 5.0 ul $CaCl_2$ 450 ul EDTA blood 50 ul collagen | 194 | 80 | 33 | 20 | 90% |
| 20 ul $CaCl_2$ 450 ul EDTA blood 50 ul collagen | 240 | 224 | 218 | 214 | 11% |
| 35 ul $CaCl_2$ | 270 | 194 | 95 | 182 | 12% |

EXAMPLE 3

Optimal Citrate Concentration for Platelet Aggregation

Citrate is added to the EDTA-anticoagulated blood samples containing calcium chloride. The calcium chloride is added to neutralize the effect of EDTA on the platelets whereas the citrate is added to avoid clotting.

Five different concentrations of sodium citrate are added to an equal number of tubes containing 450 microliters of EDTA-anticoagulated blood containing 5 microliters of 0.5 M calcium chloride. The platelet counts are obtained on a Cell Dyn 900 counter. The results of the experiment are shown in Table 3 below.

TABLE 3

| Citrate Concentration for Platelet Aggregation | | | | | |
|---|---|---|---|---|---|
| Sodium Citrate (ul) | Platelet Count ($\times 10^3/mm^3$) | | | | Aggregation (%) |
| | 0 | 2 min | 4 min | 6 min | |
| 5 | 261 | Blood-Clotted | | | |
| 10 | 261 | 81 | 53 | 40 | 85% |
| 20 | 261 | 208 | 146 | 123 | 53% |
| 30 | 261 | 261 | 280 | 268 | 0% |

Each tube contains 5 microliters of 0.5 M $CaCl_2$, 450 microliters of $K_3$-EDTA whole blood, 50 microliters of collagen (Sigma) and the indicated amount of 0.5 M sodium citrate.

EXAMPLE 4

Preparation of the Platelet Aggregation Reagent of the Invention

Various samples containing solutions of proportioned amounts of calcium chloride and sodium citrate are placed in separate test tubes and diluted ten fold, e.g., 10 microliters to 100 microliters, an aggregating amount of collagen added and the tubes are then lyophilized and sealed. These tubes are then utilized for the other experiments.

EXAMPLE 5

Platelets Stability in EDTA-anticoagulated Blood at 4° C. and 25° C.

EDTA-anticoagulated blood can be stored for several hours without loss of platelets through aggregation or loss of platelet function. The recovery of platelet function in EDTA-anticoagulated blood is studied with 8 different normal subjects at various intervals as can be seen on the leftmost column of Table 4 below.

Initial platelet count is 178,000. 5 microliters of 0.5 M $CaCl_2$ and 10 microliters of 0.5 M sodium citrate are added to 450 microliters of microliters of ADP (Sigma). When reconstituted the concentration is 0.2 mmol/liter. The percent aggregation values are those at 6 minutes. The values obtained on the Cell Dyn counters are calculated as in Table 1. The values reported for the aggregometer are obtained by assaying on a Bio Data PAP-3 instrument.

A complete recovery of platelet activity is demonstrated up to four hours after blood collection.

TABLE 4

Platelet Stability in $K_3$-EDTA at 4° and 25° C.

| | Cell Dyn 900 Platelet Count ($10^3/mm^3$) | | | | Aggregation % | |
|---|---|---|---|---|---|---|
| | 2 min | 4 min | 6 min | Cell Dyn | Aggregometer |
| 0 | 0 | 0 | 0 | 100 | 95 |
| 1 hr | | | | | |
| 4° C. | 39 | 4 | 0 | 100 | 92 |
| 25° C. | 29 | 12 | 2 | 99 | 91 |
| 2 hr | | | | | |
| 4° C. | 19 | 8 | 4 | 99 | 91 |
| 25° C. | 55 | 24 | 11 | 93 | 87 |
| 4 hr | | | | | |
| 4° C. | 67 | 19 | 5 | 99 | 89 |
| 25° C. | 104 | 57 | 33 | 81 | 89 |
| 6 hr | | | | | |
| 4° C. | 44 | 30 | 17 | 87 | 86 |
| 25° C. | 162 | 110 | 60 | 66 | 87 |

EXAMPLE 6

Comparison of Platelet Aggregation Measured With the Invention and with an Aggregometer Platelet aggregation is measured on normal patients by the method of the present invention and compared with measurements obtained with the aggregometer method. The results of the studies are shown in Table 5 below.

The values in the table are for maximum aggregation on an aggregometer and a platelet counter. The time for maximum aggregation occurred between 1 and 8 minutes for all tests. Lyophilized tubes containing 50 microliters of each reagent, 5 microliters of 0.5 M $CaCl_2$ and 10 microliters of 0.5 M sodium citrate is added to 450 microliters of $K_3$-EDTA whole blood for platelet counting with the Cell Dyn 900 counter. The reagents are all Sigma:ADP at a concentration of 0.2 mmol/liter, collagen at a concentration of 2 mg/ml, epinephrine at a concentration of 0.1 mmol/liter and ristocetin at a concentration of 15 mg/ml. The Bio-Data PAP-3 aggregometer was used with the same Sigma reagents described above.

A good agreement is seen between the two methods for all "agonists", namely collagen, ADP, epinephrine and ristocetin. The data shown in Table 5 are typical of the data obtained and indicate that a good response of platelet function can usually be measured by doing a platelet count at about six minutes from addition of the blood to the reagents.

TABLE 5

Aggregometry on Cell Dyn 900 Compared with a Bio-Data Aggregometer on Normal Subjects

| | | Aggregation (%) | | | |
|---|---|---|---|---|---|
| # | Method | ADP | Collagen | Epinephrine | Ristocetin |
| 1 | Cell Dyn 900 | 100 | 74 | 35 | 92 |
| | Bio-Data | 96 | 82 | 38 | 93 |
| 2 | Cell Dyn 900 | 92 | 72 | 74 | 85 |
| | Bio-Data | 91 | 84 | 86 | 90 |
| 3 | Cell Dyn 900 | 100 | 81 | 72 | 86 |
| | Bio-Data | 84 | 78 | 76 | 85 |
| 4 | Cell Dyn 900 | 100 | 22 | 72 | 100 |
| | Bio-Data | 90 | 22 | 69 | 94 |
| 5 | Cell Dyn 900 | 87 | 87 | 36 | 95 |
| | Bio-Data | 86 | 83 | 23 | 91 |
| 6 | Cell Dyn 900 | 100 | 94 | 99 | 100 |
| | Bio-Data | 99 | 88 | 97 | 97 |
| 7 | Cell Dyn 900 | 100 | 100 | 77 | 100 |
| | Bio-Data | 100 | 93 | 91 | 100 |
| 8 | Cell Dyn 900 | 100 | 100 | 76 | 95 |
| | Bio-Data | 100 | 94 | 92 | 99 |
| 9 | Cell Dyn 900 | 100 | 93 | 84 | 84 |
| | Bio-Data | 92 | 86 | 87 | 90 |
| 10 | Cell Dyn 900 | 92 | 90 | 89 | 93 |
| | Bio-Data | 100 | 100 | 98 | 100 |

The values shown in the table correspond to the maximum aggregation on an aggregometer and a platelet counter. The time for maximum aggregation occurred between 1 and 8 minutes for all tests.

Lyophilized tubes containing 50 microliters of each reagent, 5 microliters of 0.5 M $CaCl_2$, and 10 microliters of 0.5 M sodium citrate are added to 450 microliters of $K_3$-EDTA whole blood for the method of the invention (Cell Dyn 900). The reagents are all trom Sigma:ADP is used at a concentration of 0.2 mmol/liter, collagen at a concentration of 2 mg/ml, epinephrine at a concentration of 0.1 mmol/liter and Ristocetin at a concentration of 15 mg/ml. The same Sigma reagents described above are used for the test with the aggregometer method (Bio-Data PAP-3).

EXAMPLE 7

Measurement of Platelet Aggregation by the Present Method and With an Aggregometer in Normal Subjects taking Aspirin This study was conducted with normal subjects before and after ingesting two 325 mgs aspirins 3-4 times daily for seven days. The results of this study are shown in Table 6 below.

A decrease in aggregation following aspirin ingestion is seen when platelet function is measured with the present method, both when collagen and epinephrine are used to induce the aggregation. The aggregometer (Bio-Data) method did not indicate a decrease in aggregation with the collagen reagent. However, the continuous stirring of the plasma during the measurements with the aggregometer seems to enhance the ability of the platelets to aggregate. If the present method is conducted by continually mixing the sample, no decrease in aggregation (94% aggregation) is observed. The differences are therefore attributed to the mixing required by the aggregometer method.

TABLE 6

Aggregometry on Cell Dyn 900 Compared with a Bio-Data
Aggregometer on Normal Subject Taking Aspirin

| | % Aggregation | | | |
|---|---|---|---|---|
| | ADP | Collagen | Epinephrine | Ristocetin |
| Pre-aspirin | | | | |
| Cell Dyn 900 | 100 | 100 | 76 | 95 |
| Bio-Data | 100 | 94 | 92 | 99 |
| Post-aspirin | | | | |
| Cell Dyn 900 | 100 | 34 | 30 | 100 |
| Bio-Data | 96 | 95 | 41 | 86 |

EXAMPLE 8

Platelet Aggregation Measured in Abnormal Subjects by the Present Method and with an Aggregometer Platelet aggregation is measured by the present method and with an aggregometer on whole blood samples from abnormal subjects. The results obtained in this study are shown in Table 7 below.

The first set of results are obtained from a patient with multiple myeloma. The patient is taking darvocet and ulcer medication.

Patients diagonosed with multiple myeloma are known to show decreased platelet aggregation with "agonists" such as collagen and epinephrine. A reduction in platelet aggregation is observed with the system of the invention.

However, the data obtained with the standard aggregometer method does not show a reduction. If the method of this invention is conducted by continually mixing the sample as is done on the aggregometer, no reduction of aggregation is observed with collagen (94% aggregation) and a minor reduction is observed with epinephrine (56% aggregation). This is attributed to a loss of sensitivity occurring in the aggregometer due to the required constant mixing.

The second set of data correspond to a subject also suffering from multiple myeloma. The patient, however, is not taking any drug therapy at the time. Decreased aggregation is also seen with collagen and ephinephrine as expected.

TABLE 7

Platelet Aggregation measured in Abnormal.

| | % Aggregation | | | |
|---|---|---|---|---|
| | ADP | Collagen | Epinephrine | Ristocetin |
| Cell Dyn 900[1] | 92 | 67 | 37 | 84 |
| Bio-Data | 86 | 88 | 83 | 86 |
| Cell Dyn 900[2] | 100 | 34 | 32 | 100 |
| Bio-Data | 99 | 58 | 22 | 86 |

[1]The above data are obtained from a subject with multiple myeloma. The patient is taking darvocet and ulcer medication.
[2]This subject also has multiple myeloma. The patient is not currently on any drug therapy. This patient also shows decreased aggregation with collagen and epinephrine as expected.

EXAMPLE 9

Prothrombin Time (P.T.) and Partial Thromboplastin Time (P.T.T.)

This example evaluates the use of the present invention for doing a prothrombin time (P.T.) test and partial thromboplastin time (P.T.T.).

Blood is collected in a sodium citrate tube as is usual for P.T. tests and placed on ice. Another blood sample is collected in a $K_3$-EDTA tube. The EDTA-anticoagulated blood (4.0 ml) is added to 40 microliters of 0.5 M $CaCl_2$ and 80 microliters of 0.5 M sodium citrate and mixed. The tube is then placed on ice.

Both the sodium citrate and $K_3$-EDTA blood samples are run on an MLA ® Electra 700 Automatic Coagulation Timer. The times obtained are

| | P.T. | P.T.T. | Normal Range |
|---|---|---|---|
| $K_3$-EDTA | 12 seconds | 28 seconds | P.T. = 10–13 sec |
| citrate | 12 seconds | 27 seconds | P.T.T. = 22–35 sec |

This result indicates that blood for prothrombin time may be collected in a $K_3$-EDTA and "converted" for use by the present procedure.

The invention now being tully described, it will be apparent to one with ordinary skill in the art that many changes and modications can be made thereto without departing from the spirit or scope of the invention as set torth herein.

What is claimed is:

1. A platelet aggregation reagent for EDTA-anticoagulated blood, said reagent comprising
    calcium chloride,
    sodium citrate, and
    a platelet-aggregating agent;
the calcium and the citrate being present in a proportion of about 1.5 micromoles:5 micromoles to about 7.5 micromoles:2.5 micromoles per at least about a platelet aggregating amount of the agent.

2. The platelet aggregation reagent of claim 1, wherein
    the platelet aggregating agent is selected from the group consisting of adenosine diphosphate, collagen, epinephrine, ristocetin, adrenaline, thrombin and arachidonic acid.

3. The platelet aggregation reagent of claim 1, in solid form.

4. The platelet aggregation reagent of claim 3 as a lyophilized solid.

5. The platelet aggregation agent of claim 2, wherein
    the adenosine diphosphate is present in an amount of about 10 micromoles to 30 micromoles.

6. The platelet aggregation reagent of claim 2, wherein
    the collagen is present in an amount of about 0.1 mg/ml to 0.4 mg/ml of the reagent.

7. The platelet aggregation reagent of claim 2, wherein
    the epinephrine is present in an amount of about 5 micromoles to 20 micromoles.

8. The platelet aggregation reagent of claim 2, wherein
    the ristocetin is present in an amount of about 1.0 mg/ml to 1.5 mg/ml of the reagent.

9. The platelet aggregation reagent of claim 1, wherein
    the calcium chloride and the sodium citrate are present in a proportion of about 2. 5 micromoles:5 micromoles.

10. A platelet aggregation reagent container for EDTA-anticoagulated blood, comprising
    an elongated container suitable for use in a platelet counter containing a reagent comprising
    about 1.5 micromoles to 7.5 micromoles of calcium chloride; and
    about 2.5 micromoles to 5.0 micromoles of sodium citrate; and at least about a platelet aggregating amount of a platelet-aggregating agent.

11. The reagent container of claim 10, wherein the platelet-aggregating agent is selected from the group consisting of adenosine diphosphate, collagen, epinephrine, ristocetin, adrenaline, thrombin and arachidonic acid.

12. The reagent container of claim 10, wherein the reagent contained in the container is in solid form.

13. The reagent container of claim 12, wherein the reagent contained in the container is a lyophilized solid.

14. The reagent container of claim 3, wherein the container is sealed.

15. The reagent container of claim 10 in disposable form.

16. A method of determining platelet aggregation in EDTA-anticoagulated blood, said method comprising
   (a) counting the number of platelets contained in an EDTA-anticoagulated blood sample to obtain an initial platelet count (IC);
   (b) contacting the sample with calcium chloride, sodium citrate and a platelet-aggregating agent in proportions of at least about a platelet aggregating amount of the agent per about 450 microliters of sample, about 1.2 micromoles to 7.5 micromoles of the calcium and about 2.5 micromoles to 5.0 micromoles of the citrate;
   (c) counting the number of platelets contained in the thus contacted sample at desired intervals for a period of about 1 min to 10 min;
   (d) selecting the maximum platelet count (MC) obtained in step (c); and
   (e) calculating platelet aggregation (PA) from the equation $$PA = (IC - MC)/IC.$$

17. The method of claim 16, wherein step (e) is conducted by calculating percent platelet aggregation (%PA) from the equation $$\% PA = [(IC - MC) \times 100]/IC.$$

18. The method of claim 16, wherein the platelet-aggregating agent is selected from the group consisting of adenosine diphosphate, collagen, epinephrine, ristocetin, adrenaline, thrombin and arachidonic acid.

19. The method of claim 18, wherein the adenosine diphosphate is present in an amount of about 10 micromoles to 30 micromoles.

20. The method of claim 18, wherein the collagen is present in an amount of about 0.1 mg/ml to 0.4 mg/ml of the contacted sample, the calcium chloride, the sodium citrate and the platelet-aggregating agent.

21. The method of claim 18, wherein the epinephrine is present in an amount of about 5 micromoles to 20 micromoles.

22. The method of claim 18, wherein the ristocetin is present in an amount of about 1.0 mg/ml to 1.5 mg/ml of the contacted sample, the calcium chloride, the sodium citrate and the platelet-aggregating agent.

* * * * *